United States Patent [19]

Lin

[11] Patent Number: 5,186,402
[45] Date of Patent: Feb. 16, 1993

[54] INJECTION NEEDLE DISPOSAL DEVICE

[76] Inventor: Yung-Jyi Lin, c/o Hung Hsing Patent Service Center P.O. Box 55-1670, Taipei (10477), Taiwan

[21] Appl. No.: 822,893

[22] Filed: Jan. 21, 1992

[51] Int. Cl.⁵ ............................................. B02C 19/12
[52] U.S. Cl. ........................................ 241/55; 241/99; 241/296; 241/606; 51/128; 51/170 T; 51/227 H
[58] Field of Search .................. 241/55, 99, 296, 298, 241/606; 51/128, 170 T, 227 H

[56] References Cited

U.S. PATENT DOCUMENTS

| | | | |
|---|---|---|---|
| 2,713,760 | 7/1955 | Dunham et al. | 51/227 H |
| 3,043,060 | 7/1962 | Bell et al. | 51/128 X |
| 3,589,276 | 6/1971 | Swallert | 241/606 X |
| 3,958,765 | 5/1976 | Musselman | 241/99 |
| 4,520,964 | 6/1985 | Rössler | 241/55 |
| 4,930,264 | 6/1990 | Huang | 51/170 T |
| 4,971,261 | 11/1990 | Solomons | 241/606 X |

Primary Examiner—Frank T. Yost
Assistant Examiner—Raymond D. Woods

[57] ABSTRACT

An injection needle disposal device includes a housing, a grinding wheel having a plurality of impellers of an exhaust fan surrounding the grinding wheel, a main driving motor rotating the grinding wheel and the impellers, a positioning disk secured on the housing for inserting an injection needle secured with a syringe into the housing to be ground by the grinding wheel and the dust of the ground needle is sucked by the impellers and exhausted outwardly to be collected by a collection bag connected with the housing.

11 Claims, 5 Drawing Sheets

INJECTION NEEDLE DISPOSAL DEVICE

BACKGROUND OF THE INVENTION

Jack R. Sorwick et al. disclosed a syringe disposal apparatus and method in their U.S. Pat. No. 4,905,916 including a portable collection unit and a process unit. The collection unit has an infeed mechanism to allow syringes to be introduced into the collection unit; and an interlock mechanism suitable for removably securing the collection unit to the processing unit and emptying the syringes from the collection unit into the processing unit. The processing unit contains an interlock mechanism suitable to activating the collection unit interlock mechanism; a grinder suitable for grinding the syringes into particles of metal and plastic; and a crucible assembly suitable for heating these particles above the melting point of plastic, and then cooling to produce a solid puck of plastic in which the metal particles are suspended and encapsulated.

However, such a syringe disposal means may require a complex mechanism and structure to possibly increase its production cost and maintenance problem. It should provide means for separating plastic material of the syringe part from metal powder of the needle part so that it is uneconomic and unsuitable for a small-scale disposal of syringe such as in a private clinic or small hospital.

Therefore, the present inventor invents a compact unit for the disposal of syringe needle for economic purpose.

SUMMARY OF THE INVENTION

The object of the present invention is to provide an injection needle disposal device with economic construction cost including a housing, a grinding wheel having a plurality of impellers of an exhaust fan surrounding the grinding wheel, a main driving motor rotating the grinding wheel and the impellers, a positioning disk secured on the housing for inserting an injection needle secured with a syringe into the housing to be abrasively around by the grinding wheel and the dust of the ground needle are sucked by the impellers and exhausted outwardly to be collected by a collection bag connected with the housing.

DETAILED DESCRIPTION

Figure 1:
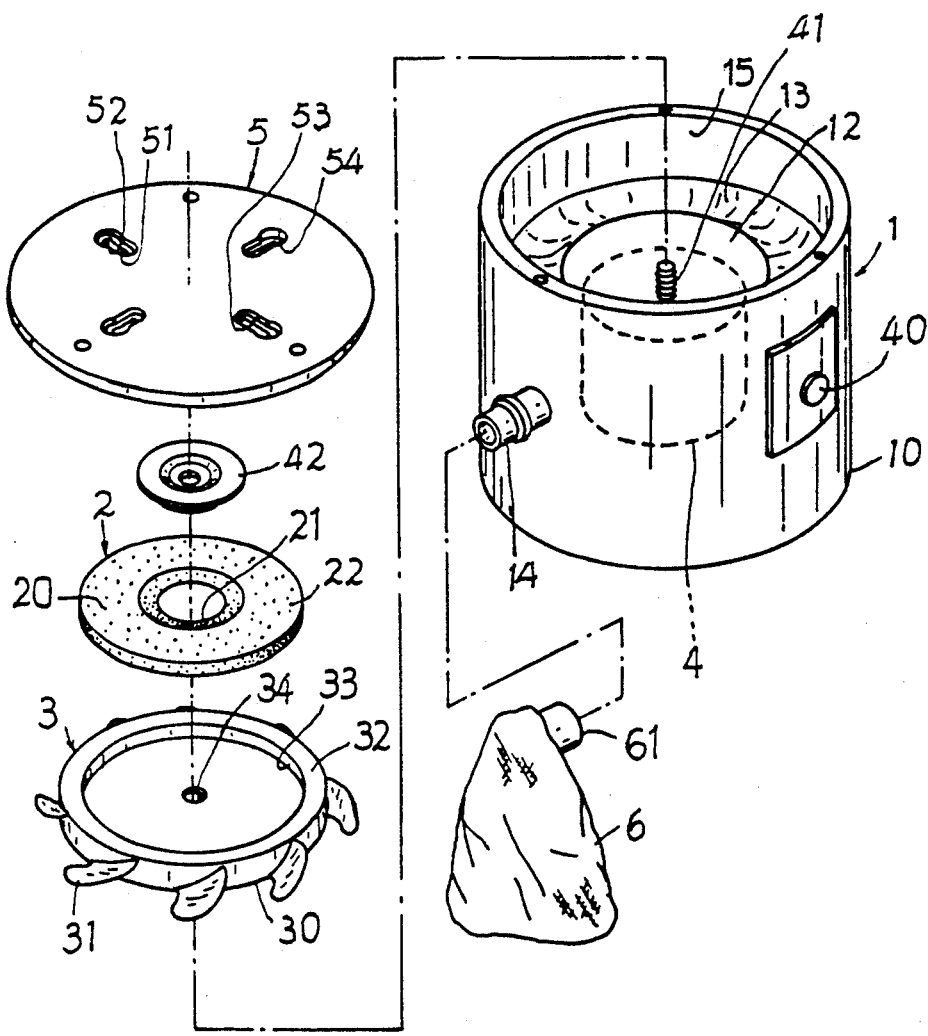
FIG. 1 is an illustration showing all elements in construction of the present invention.

As shown in FIGS. 1-4, the present invention comprises: a housing 1, a grinding wheel 2, an exhaust fan means 3, a main driving motor 4, a positioning disk 5, and a collection bag 6.

The housing 1 includes: a housing wall or cylindrical wall portion 10, a bottom plate 11 secured on a bottom portion of the housing or cylindrical wall portion 10, a partition plate 12 formed in an upper portion of the housing or the cylindrical wall portion 10, an annular groove 13 annularly formed in an outer periphery of the partition plate 12, a discharge duct 14 mounted on the housing or cylindrical wall portion 10 and communicated with the annular groove 13, and a grinding chamber 15 formed in between the partition plate 12 and the positioning disk 5 sealably secured on an uppermost edge portion of the housing or cylindrical wall portion 10 of the housing 1.

Figure 3:
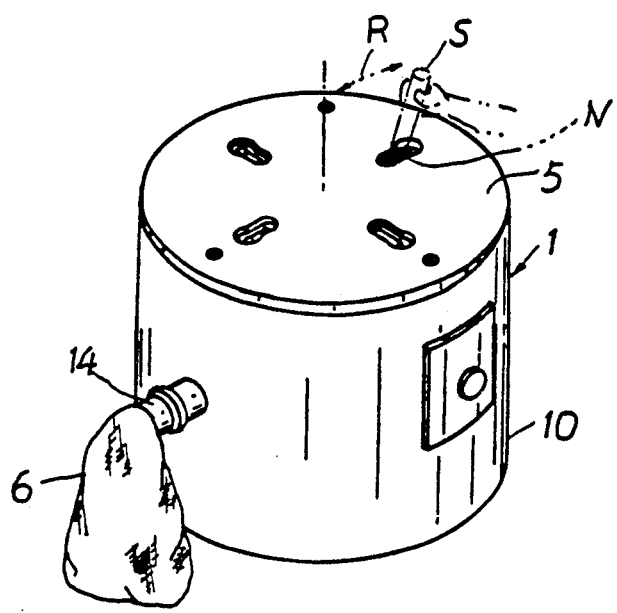
FIG. 3 is a perspective view of the present invention.

The grinding wheel 2 may be selected from a grindstone wheel or other wheels having abrasively grinding surface for grinding an injection needle N fixed on a syringe S as shown in FIG. 3.

The exhaust fan means 3 includes a plurality of impellers 31 circumferentially formed on a periphery extension portion 32 of a circular retaining disk 30, a circular recess 33 recessed in the circular retaining disk 30 engageable with an outer perimeter 22 of the grinding wheel 2, and a central hole 34 of the circular retaining disk 30 for mounting the circular retaining disk 30 on a main shaft 41 of the main driving motor 4.

Figure 2:
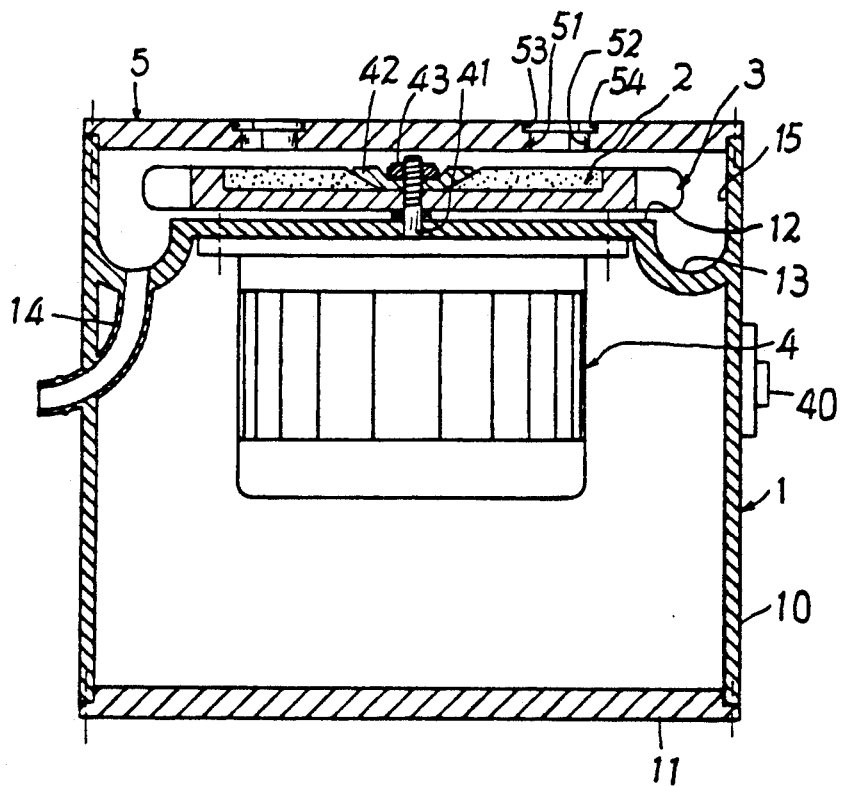
FIG. 2 is a sectional drawing of the present invention.

The grinding wheel 2 having a central hole 21 formed in a center of the grinding wheel 2 is overlapped on the circular retaining disk 30 of the exhaust fan means 3 and secured on the main shaft 41 of the main driving motor 4 by a washer 42 and a nut 43 as shown in FIG. 2 so that the grinding wheel 2 and the exhaust fan means 3 are superimposedly mounted on and perpendicular to the main shaft 41 of the main driving motor 4 above the partition plate 12 and within the grinding chamber 15 of the housing.

Figure 4:
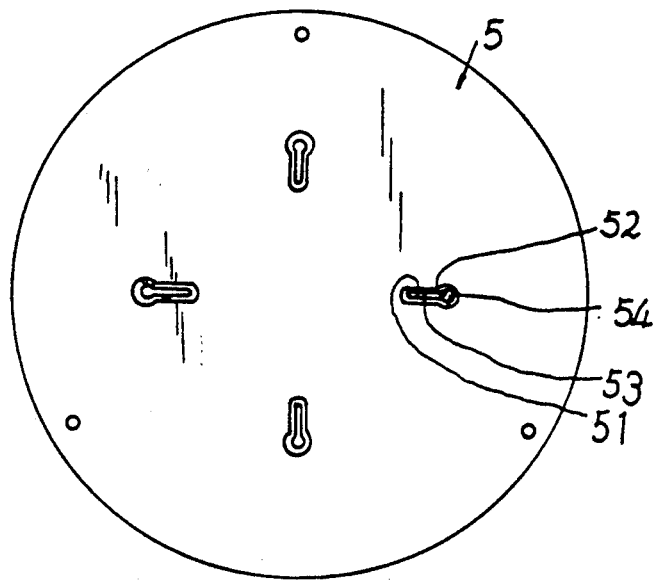
FIG. 4 is a top view of the positioning disk of the present invention.

The positioning disk 5 as shown in FIGS. 2 and 4 includes a plurality of needle slits 51 radially formed in the positioning disk 5 proximate to the grinding wheel 2, each needle slit 51 connected and communicated with a large needle hole 52 formed in one end portion of the needle slit 51 for inserting a needle with larger diameter than that of a needle with small diameter insertable in the slit 51.

Each needle slit 51 is formed through a thickness of the positioning disk 5 and is enlarged to form a syringe slot 53 on an upper portion of the needle slit 51 having a width wider than a width of the needle slit 51 allowing an insertion of a syringe S into the syringe slot 53, but precluding an insertion of the syringe S into the needle slit 51. A large syringe socket 54 is disposed around and positioned on an upper portion of the large needle hole 52 having a diameter of the syringe socket 54 larger than that of the large needle hole 52 for inserting a syringe secured with the larger needle insertable into the large needle hole 52.

When using the present invention, a push button of power switch 40 formed on the housing 1 is actuated to start the running of the main motor 4 to rotate the grinding wheel 2 and the exhaust-fan impellers 31. An injection needle N secured on the syringe S is inserted through the slit 51 to contact a grinding surface 20 horizontally formed on the wheel 2 so that the needle may be ground into dust by the rotating grinding wheel 2. The dusts of the ground needle are then centrifugally exhausted by the exhaust-fan impellers 31, guided by the annular groove 13 and discharged through the duct 14 to be collected into the collection bag 6 having an inlet connector 61 of the bag 6 connected with the duct 14 formed on the housing 1. The needle N is preferably inclinedly inserted into the disk 5 to be in a tilting contact with the grinding surface 20 to prevent a deep spot digging or wearing on the grinding surface. The needle N may be radially moved (R) as grasped by an operator's hand as shown in FIG. 3 for manually grinding the needle for a hygienic disposal thereof.

Figure 5:
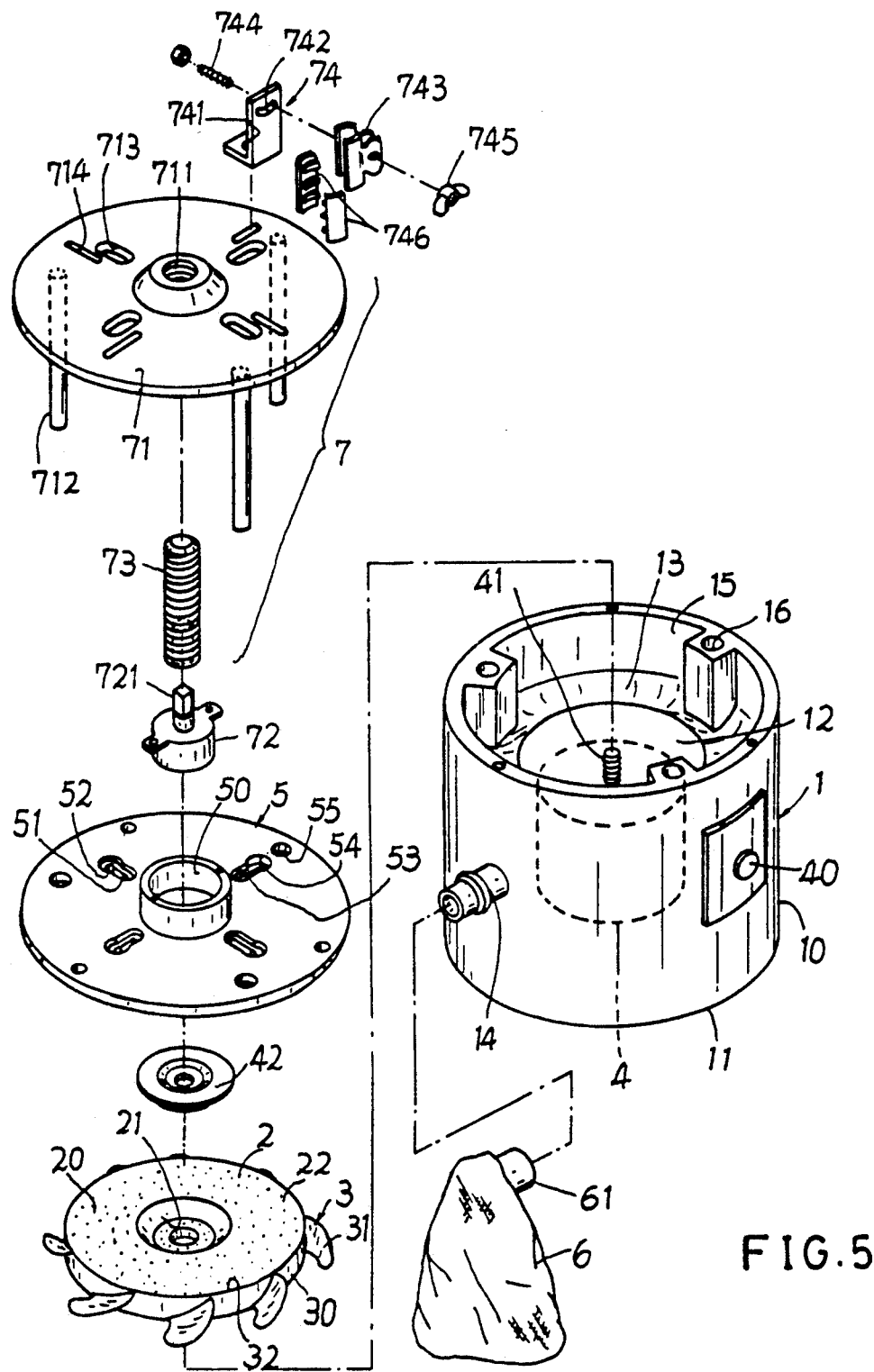
FIG. 5 is an illustration of all elements of another preferred embodiment of the present invention.
Figure 6:
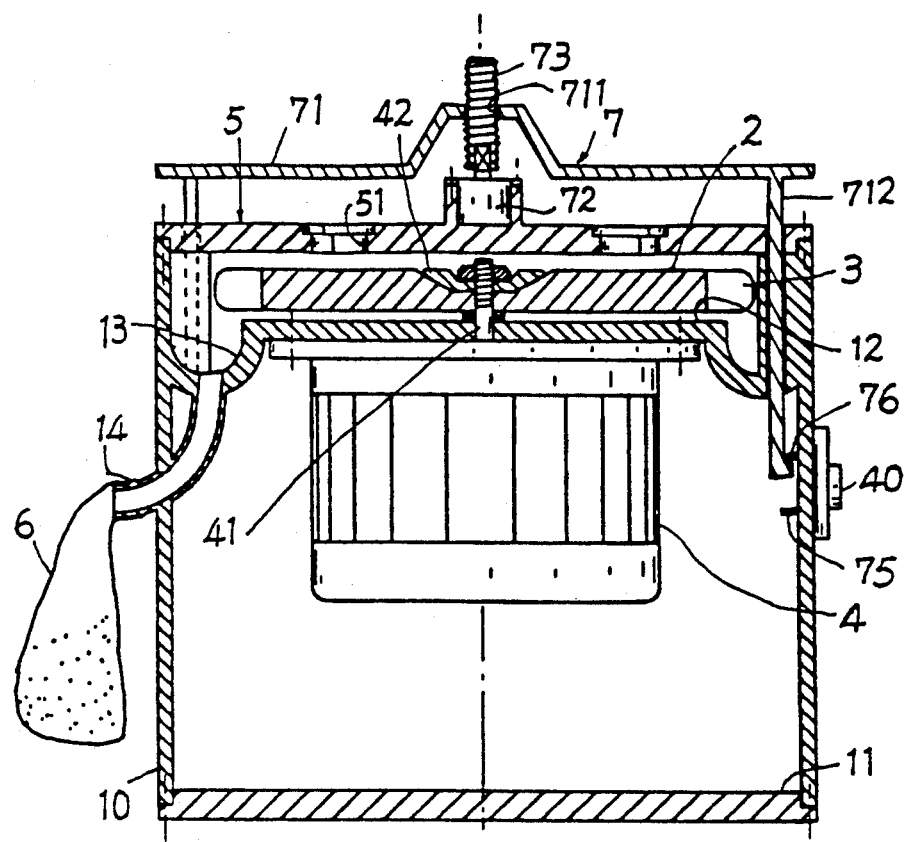
FIG. 6 is a sectional drawing of the present invention as shown in FIG. 5.
Figure 7:
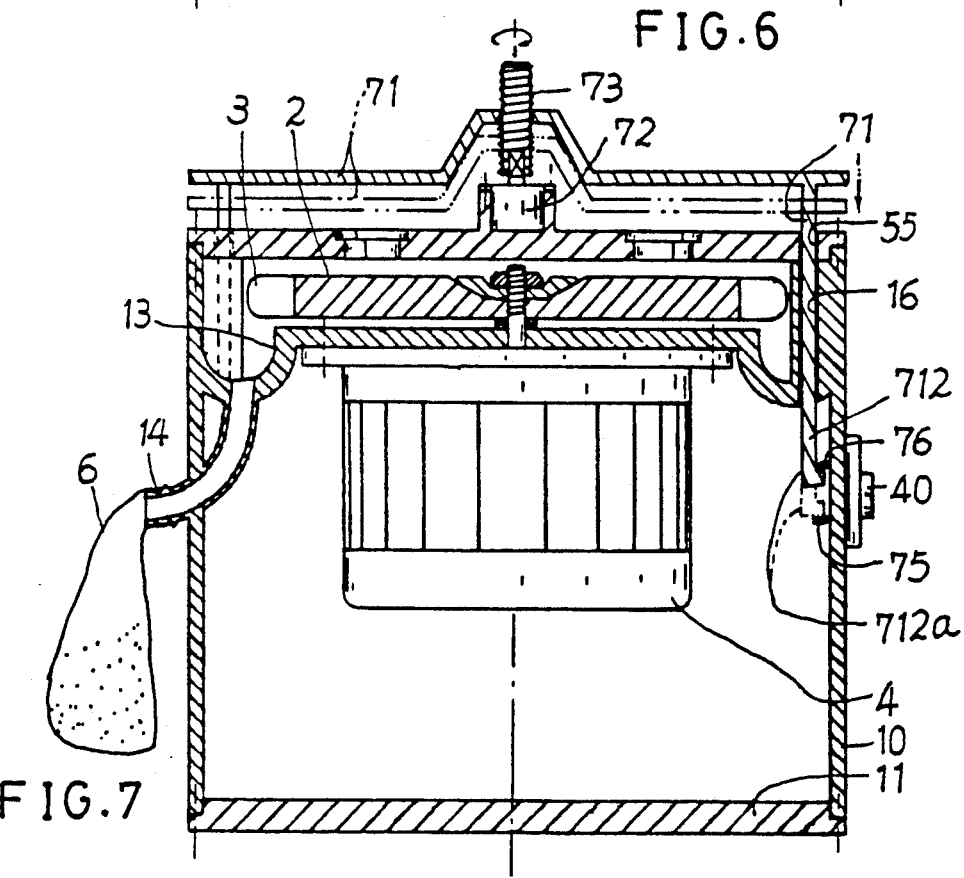
FIG. 7 shows a downward movement of a movable disk of the embodiment as shown in FIG. 5.

As shown in FIGS. 5–7, another preferred embodiment of the present invention further comprises: an automatic syringe moving means 7 formed on an upper portion of the positioning disk 5 including: a movable disk 71, an up-and-down driving means 72, a driving bolt 73 secured with the driving means 72 for lowering or rising the disk 71, a plurality of syringe holding means 74 adjustably mounted on the disk 71 for holding syringe thereon, a lower-dead-point micro switch 75 and an upper-dead-point micro switch 76 for operatively limiting a downward stroke and an upward stroke of the disk 71.

The movable disk 71 includes: a female-threaded hole 711 formed in a central portion of the movable disk 71, a plurality of guiding stems 712 vertically protruding downwardly from the movable disk 71 reciprocatively held in a plurality of corresponding guiding sockets 16 longitudinally formed in an inside wall of the cylindrical wall portion 10 of the housing 1 and reciprocatively passing through a plurality of guiding holes 55 formed in the positioning disk 5, a plurality of upper syringe slots 713 radially formed in the movable disk 71 projectively corresponding to the syringe slots 53 radially formed in the positioning disk 5 for inserting a syringe and needle held on each syringe holding means 74 through the upper syringe slot 713 to touch the grinding wheel 2, and a plurality of adjusting slots 714 each adjusting slot 714 radially formed in the movable disk juxtapositional to each upper syringe slot 713.

The up-and-down driving means 72 is an up-and-down driving motor 72 which is mounted in a motor socket 50 formed in a central portion of the positioning disk 5 having a spindle 721 vertically secured with the driving bolt 73 having male threads formed on the bolt 73 engageable with the female-threaded hole 711 formed in the movable disk 71. The motor 72 is forwardly rotated to rotate the bolt 73 to lower the disk 71, and reversely rotated to counter rotate the bolt to raise the disk 71.

Each syringe holding means 74 includes: a holding bracket 741 slidably adjustably mounted on the movable disk 71 by a screw (not shown) along each adjusting slot 714 formed in the movable disk 71, a syringe clamp 743 having a pair of clips resiliently clamping a syringe on the clamp 743 pivotally secured on the bracket 741 by an adjusting screw 744 passing through an arcuate groove 742 formed in the bracket 741 and locked by a nut 745, and a pair of elastomer linings 746 respectively packed on the two clips of the clamp 743 for firmly clamping the syringe thereon.

The micro switch 75 mounted inside the cylindrical wall portion 10 will be operatively actuated by a lower depression portion 712a formed on a bottom portion of each guiding stem 712 to stop the running of the two motors 72, 4 until the needle on the syringe is ground to its minimum length and the movable disk 71 has reached its lowermost stroke of downward movement during a forward rotation of the driving motor 72 to lower the disk 71 by initating the power switch 40.

The power switch 40 may be operated to reversely rotate the driving motor 72 to raise the disk 71 and each guiding stem 712 until the upper-dead-point micro switch 76 mounted inside the wall 10 above the switch 75 is actuated by the depression portion 712a, whereby the motors 4, 72 will then be stopped.

Figure 8:
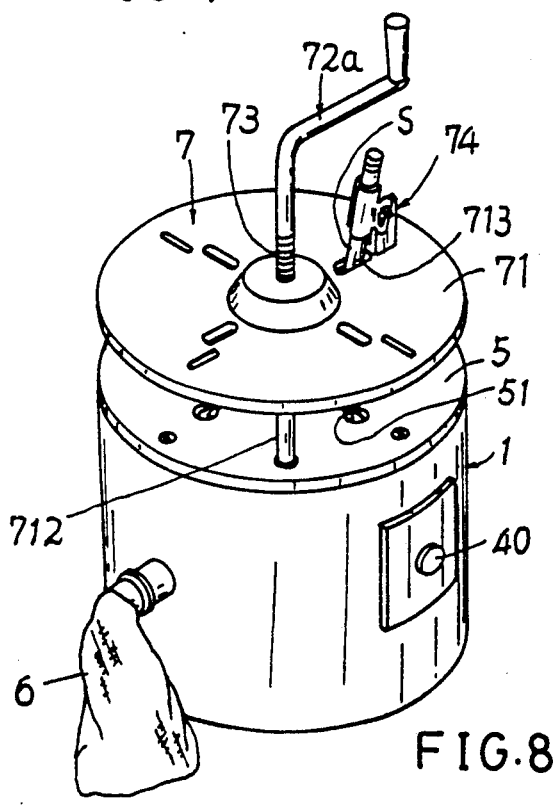
FIG. 8 shows still another preferred embodiment of the present invention.

The up-and-down driving means 72 may be modified to be a crank handle 72a as shown in FIG. 8 in which the handle 72a is secured to the driving bolt 73 and protruded upwardly and outwardly to be manually rotated by an operator for rotating the bolt 73 for either lowering the movable disk 71 for grinding the neddle or raising the disk ready for next grinding operation.

As shown in FIG. 5, the grinding wheel 2 and the exhaust fan means 3 are combined by embedding a peripheral portion 22 of the grinding wheel 2 into a circular extension 32 of the exhaust fan means 3 having a plurality of impellers 31 radially secured to and disposed about the circular extension 32 formed on a circular disk 30 of the fan means 3. The wheel 2 and fan means 3 are coaxially mounted on the main shaft 41 of the main motor 4.

I claim:

1. An injection needle disposal means comprising:
a housing, a grinding wheel having a plurality of impellers of an exhaust fan means surrounding the grinding wheel rotatably mounted in said housing, a main driving motor operatively rotating the grinding wheel and the impellers, a positioning disk secured on the housing for inserting an injection needle secured on a syringe into the housing to be abrasively ground by the grinding wheel, said housing including: a housing wall portion, a bottom plate secured on a bottom portion of the housing wall portion, a partition plate formed in an upper portion of the housing wall portion, an annular groove annularly formed in an outer periphery of the partition plate, a discharge duct mounted through the housing wall portion and communicating with the annular groove, and a grinding chamber formed in between the partition plate and the positioning disk sealably secured on an uppermost edge portion of the housing wall portion of the housing; said exhaust fan means and said grinding wheel being rotatably mounted in said partition plate within said grinding chamber; and
said exhaust fan means including said plurality of impellers circumferentially formed on a periphery extension portion of a circular retaining disk, a circular recess recessed in the circular retaining disk engageable with an outer perimeter of the grinding wheel, and a central hole of the circular retaining disk for mounting the circular retaining disk on a main shaft of the main driving motor, whereby upon a rotation of the grinding wheel and the fan means, dusts from a ground needle are sucked by the impellers and exhausted outwardly to be collected by a collection bag connected to the housing.

2. A needle disposal means according to claim 1, wherein said grinding wheel having a central hole formed in a center of the grinding wheel is overlapped on the circular retaining disk of the exhaust fan means and secured on the main shaft of the main driving motor by a washer and a nut so that the grinding wheel and the exhaust fan means are superimposedly mounted on and perpendicular to the main shaft of the main driving motor above the partition plate and within the grinding chamber of the housing.

3. A needle disposal means according to claim 1, wherein said positioning disk includes a plurality of needle slits radially formed in the positioning disk proximate to the grinding wheel, each said needle slit connected with and communicating with a large needle hole formed in one end portion of the needle slit for inserting a needle with larger diameter than that of a needle with small diameter insertable in the needle slit.

4. A needle disposal means according to claim 3, wherein each said needle slit is formed through a thickness of the positioning disk and is enlarged to form a syringe slot on an upper portion of the needle slit having a width wider than a width of the needle slit allowing an insertion of a syringe into the syringe slot, but precluding an insertion of the syringe into the needle slit; a large syringe socket disposed around and positioned on an upper portion of the large needle hole having a diameter of the syringe socket larger than that of the large needle hole for inserting a syringe secured with the larger diameter needle insertable into the large needle hole.

5. A needle disposal means according to claim 1, wherein said positioning disk on said housing is further provided with an automatic syringe moving means on an upper portion of the positioning disk, which includes: a movable disk, an up-and-down driving means, a driving bolt secured with the driving means for lowering or raising the movable disk, and a plurality of syringe holding means adjustably mounted on the movable disk for holding syringes thereon, whereby upon a lowering of the movable disk, a syringe needle is lowered to be ground by said grinding wheel for disposal of the needle.

6. A needle disposal means according to claim 5, wherein said movable disk includes: a female-threaded hole formed in a central portion of the movable disk, a plurality of guiding stems vertically protruding downwardly from the movable disk reciprocatively held in a plurality of corresponding guiding sockets longitudinally formed in an inside wall of a cylindrical wall portion of the housing, a plurality of upper syringe slots radially formed in the movable disk projectively corresponding to syringe slots radially formed in the positioning disk for inserting a syringe and needle held on each said syringe holding means through the upper syringe slot to touch the grinding wheel, and a plurality of adjusting slots each said adjusting slot radially formed in the movable disk juxtapositional to each upper syringe slot.

7. A needle disposal means according to claim 6, wherein each said syringe holding means inclues: a holding bracket slidably adjustably mounted on the movable disk by a screw along each said adjusting slot formed in the movable disk, a syringe clamp having a pair of clips resiliently clamping a syringe on the clamp pivotally secured on the bracket by an adjusting screw passing through an arcuate groove formed in the bracket and locked by a nut for adjusting a tilting angle of the syringe clamped on said holding means, and a pair of elastomer linings respectively packed on the two clips of the clamp for firmly clamping the syringe thereon.

8. A needle disposal means according to claim 5, wherein said up-and-down driving means is an up-and-down driving motor which is mounted in a motor socket formed in a central portion of the positioning disk having a spindle vertically secured with the driving bolt having male threads formed on the bolt engageable with a female-threaded hole formed in the movable disk, said up-and-down driving motor being forwardly rotated to rotate the driving bolt to lower the movable disk, and reversely rotated to counter rotate the driving bolt to raise the movable disk.

9. A needle disposal means according to claim 5, wherein said automatic syringe moving means further comprises a lower-dead-point micro switch and an upper-dead-point micro switch respectively mounted inside the cylindrical wall portion of said housing for operatively limiting a downward moving stroke and an upward stroke of said movable disk; said lower-dead-point micro switch operatively actuated to stop a running of both of said driving motors when a needle of the syringe is ground to a minimum length when lowering the movable disk; and said upper-dead-point micro switch positioned above said lower-dead-point micro switch operatively actuated to stop the running of said motors when raising said movable disk.

10. A needle disposal means according to claim 5, wherein said up-and-down driving means is a crank handle secured to the driving bolt and protruded upwardly outwardly to be manually rotated by an operator for rotating the driving bolt for lowering the movable disk for grinding the needle or raising the movable disk ready for a next grinding operation.

11. A needle disposal means according to claim 1, wherein said grinding wheel and the exhaust fan means are combined together by embedding a peripheral portion of the grinding wheel into a circular extension of the exhaust fan means having said plurality of impellers radially secured to and disposed about the circular extension which is formed on a circular disk of the fan means, said wheel and said fan means being coaxially mounted on a main shaft of the main motor.

* * * * *